US008652363B1

(12) United States Patent
Ueda et al.

(10) Patent No.: US 8,652,363 B1
(45) Date of Patent: Feb. 18, 2014

(54) COMPOUND, NEAR-INFRARED ABSORBER, AND SYNTHETIC RESIN COMPOSITION CONTAINING SAME

(75) Inventors: Naoto Ueda, Saitama (JP); Kazukiyo Nomura, Saitama (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 14/006,884

(22) PCT Filed: Apr. 9, 2012

(86) PCT No.: PCT/JP2012/059654
§ 371 (c)(1),
(2), (4) Date: Sep. 23, 2013

(87) PCT Pub. No.: WO2012/144363
PCT Pub. Date: Oct. 26, 2012

(30) Foreign Application Priority Data

Apr. 21, 2011 (JP) .................................. 2011-094813

(51) Int. Cl.
*F21V 9/04* (2006.01)
*F21V 9/06* (2006.01)
*G02B 5/22* (2006.01)
*G02B 5/26* (2006.01)
*C07D 401/00* (2006.01)

(52) U.S. Cl.
USPC ........... 252/587; 106/311; 106/400; 106/401; 546/277.4; 548/469

(58) Field of Classification Search
USPC ........ 106/311, 400, 401; 252/587; 546/277.4; 548/469
See application file for complete search history.

(56) References Cited

U.S. PATENT DOCUMENTS

2011/0012075 A1    1/2011    Nii et al.

FOREIGN PATENT DOCUMENTS

JP         2005-126549      5/2005
WO      WO 2009/123056    10/2009

OTHER PUBLICATIONS

International Search Report, PCT/JP2012/059654, Jul. 3, 2012.
Oakley, S.R. et al., "Nindigo": synthesis, coordination chemistry, and properties of indigo diimines as a new class of functional bridging ligands, Chemical Communications, vol. 46, No. 36, p. 6753-6755 (2010).
Nawn, G. et al., Redox-Active Bridging Lingands Based on Indigo Diimine ("Nindigo") Derivatives, Inorganic Chemistry, vol. 50, No. 20, p. 9826-9837 (2011). Published: Jun. 20, 2011.

*Primary Examiner* — Bijan Ahvazi
(74) *Attorney, Agent, or Firm* — Young & Thompson

(57) ABSTRACT

The present invention provides a novel boron compound that has a maximum absorption wavelength in the near-infrared light range and has low absorption in the visible ray range, and thus is excellent as a near-infrared absorber, and a near-infrared absorber and a near-infrared absorbing synthetic resin composition using the compound. The present invention specifically provides a boron compound represented by the following general formula (1), preferably a boron compound wherein $R^1$ to $R^{16}$ in the general formula (1) each represent a hydrogen atom or an alkyl group, and a near-infrared absorbing synthetic resin composition containing the boron compound as a near-infrared absorber (1) 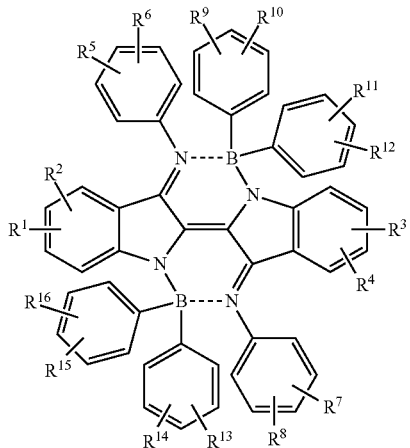
In the above-mentioned general formula (1), $R^1$ to $R^{16}$ each represent a hydrogen atom, a halogen atom, a nitro group, a cyano group, an amino group, an alkyl group having 1 to 20 carbon atoms optionally having substituents, or the like.
4 Claims, 2 Drawing Sheets

COMPOUND, NEAR-INFRARED ABSORBER, AND SYNTHETIC RESIN COMPOSITION CONTAINING SAME

TECHNICAL FIELD

The present invention relates to a novel boron compound and use thereof, and specifically relates to a novel boron compound that has absorption in the near infrared range, and thus is useful as a near-infrared absorber for information recording materials utilizing laser light (for example, optical cards, organic optical electroconductive bodies, laser thermal transfer recording, laser thermosensitive recording, laser direct plate making and the like), apparatuses for which near-infrared absorbability (or heat ray absorbability) is demanded (for example, near-infrared absorbing filter, filters for plasma displays, optical filters, optical filters for thin displays, optical filters for optical semiconductor elements, heat ray shielding films, heat ray shielding resin glasses, protective eyeglasses, secret inks, agricultural films, glasses, interior and exterior materials for automobiles, resin molded articles and the like) and the like. Furthermore, the present invention relates to a synthetic resin composition containing the compound.

BACKGROUND ART

In recent years, near-infrared absorbing dyes that have absorption in the near infrared range and thus are useful for information recording materials utilizing laser light (for example, optical cards, organic optical electroconductive bodies, laser thermal transfer recording, laser thermosensitive recording, laser direct plate making and the like), apparatuses for which near-infrared absorbability (or heat ray absorbability) is required (for example, near-infrared absorbing filters, filters for plasma displays, optical filters, optical filters for thin displays, optical filters for optical semiconductor elements, heat ray shielding films, heat ray shielding resin glasses, protective eyeglasses, secret inks, agricultural films, glasses, interior or exterior materials for automobiles, resin molded articles and the like), and the like have been increasingly demanded.

As near-infrared absorbing dyes, cyanine-based dyes, polymethine-based dyes, squarylium-based dyes, porphyrin-based dyes, metal dithiol complex-based dyes, phthalocyanine-based dyes, diimonium-based dyes, inorganic oxide particles and the like are used.

However, the near-infrared absorbabilities of these compounds are not satisfiable, and these compounds have absorption wavelengths in the visible ray range, and thus it was impossible to use them for uses for which transparency is required and applications for which coloring is not preferable. Specifically, in the cases when these near-infrared absorbing dyes are used as near-infrared absorbers, they are used by combining with synthetic resins such as thermoplastic resins in many cases, and in such cases, problems occurred in compatibility with the resins, the transparency of the resins was damaged due to the absorption wavelengths that the dyes have in the visible ray range, problems of coloring occurred, or other physical properties of the resins were damaged in many cases.

Therefore, a compound that has a maximum absorption wavelength in the near infrared range and has low absorption in the visible ray range has been demanded.

Furthermore, use of (heavy) metal elements is sometimes problematic, for the problem of environmental burden, or depending on an intended use such as the field of precise electronic materials, and thus a near-infrared absorber other than metal complexes is desired.

On the other hand, Non-patent Literature 1 describes an N indigo complex, but this is a β-diketoiminate metal (palladium) complex, and thus the finding of the present invention cannot be obtained from this complex.

CITATION LIST

Non-Patent Literature

Non-patent Literature 1: Chem. Commun, 2010, Vol. 46, pp. 6753-6755

SUMMARY OF INVENTION

Technical Problem

Therefore, the present invention aims at providing a novel boron compound that has a maximum absorption wavelength in the near-infrared light range and has low absorption in the visible ray range, and thus is excellent as a near-infrared absorber, and a near-infrared absorber using this compound. Furthermore, the present invention aims at providing a near-infrared absorbing synthetic resin composition containing the near-infrared absorber.

Solution to Problem

The present inventors intensively studied so as to solve the above-mentioned problem, and consequently found that a novel boron compound having a specific structure has a maximum absorption wavelength in the near-infrared light range and has low absorption in the visible ray range, and thus is excellent as a near-infrared absorber, and completed the present invention.

Namely, the present invention provides a boron compound represented by the following general formula (I).

[Chemical Formula 1]

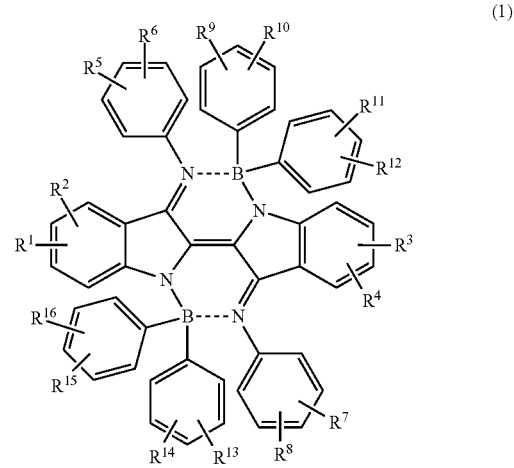

(1)

wherein $R^1$ to $R^{16}$ may be the same or different from each other, and each represent a hydrogen atom, a halogen atom, a nitro group, a cyano group, an amino group, an alkyl group having 1 to 20 carbon atoms optionally having substituents, an aryl group having 6 to 20 carbon atoms optionally having substituents, an alkoxy group having 1 to 20 carbon atoms optionally having substituents, an aryloxy group having 6 to 20 carbon atoms optionally having substituents, an arylalkyl group having 7 to 20 carbon atoms optionally having substituents, a cycloalkyl group having 5 to 12 carbon atoms optionally having substituents, an alkylthio group having 1 to 20 carbon atoms optionally having substituents, an arylthio group having 6 to 20 carbon atoms optionally having substituents, an alkylamino group having 1 to 20 carbon atoms optionally having substituents, or an arylamino group having 6 to 20 carbon atoms optionally having substituents, wherein the adjacent two groups of the groups represented by $R^1$ to $R^{16}$ may link to form a 5-membered ring or a 6-membered ring together with the carbon atom to which the respective two groups are binding.

Furthermore, the present invention provides a near-infrared absorber containing the boron compound.

Furthermore, the present invention provides a near-infrared absorbing synthetic resin composition containing the boron compound.

Furthermore, the present invention provides a near-infrared absorbing material formed of the near-infrared absorbing synthetic resin composition.

Advantageous Effects of Invention

According to the present invention, a novel boron compound that has a maximum absorption wavelength in the near-infrared light range and has low absorption in the visible ray range, and thus is excellent as a near-infrared absorber, can be provided. Furthermore, a near-infrared absorber and a near-infrared absorbing synthetic resin composition containing the boron compound can be provided.

DESCRIPTION OF EMBODIMENTS

Figure 1:
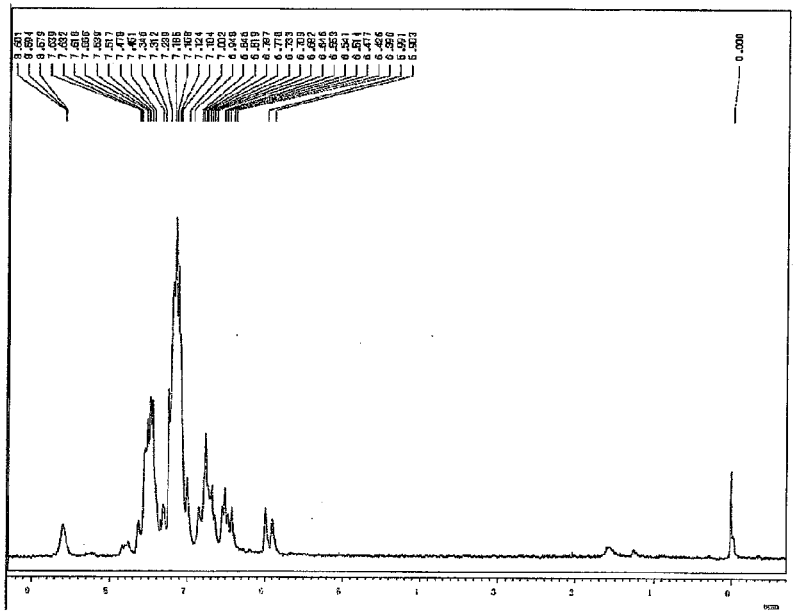
FIG. 1 shows the $^1$H-NMR chart of Compound No. 1, which is a novel boron compound of the present invention synthesized in Example 1.

Hereinafter the present invention will be explained in detail based on preferable exemplary embodiments.

Firstly, the novel boron compound of the present invention will be explained. The novel boron compound of the present invention is represented by the following general formula (I).

[Chemical Formula 2]

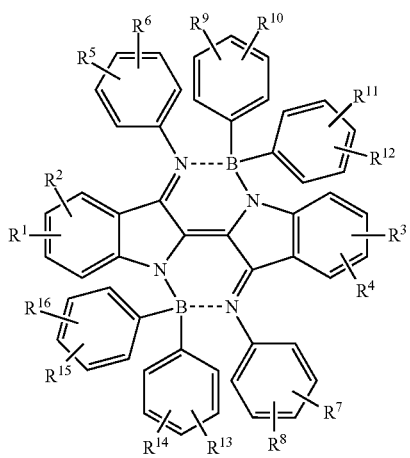

(1)

wherein $R^1$ to $R^{16}$ may be the same or different from each other, and each represent a hydrogen atom, a halogen atom, a nitro group, a cyano group, an amino group, an alkyl group having 1 to 20 carbon atoms optionally having substituents, an aryl group having 6 to 20 carbon atoms optionally having substituents, an alkoxy group having 1 to 20 carbon atoms optionally having substituents, an aryloxy group having 6 to 20 carbon atoms optionally having substituents, an arylalkyl group having 7 to 20 carbon atoms optionally having substituents, a cycloalkyl group having 5 to 12 carbon atoms optionally having substituents, an alkylthio group having 1 to 20 carbon atoms optionally having substituents, an arylthio group having 6 to 20 carbon atoms optionally having substituents, an alkylamino group having 1 to 20 carbon atoms optionally having substituents, or an arylamino group having 6 to 20 carbon atoms optionally having substituents, wherein the adjacent two groups of the groups represented by $R^1$ to $R^{16}$ may link to form a 5-membered ring or a 6-membered ring together with the carbon atom to which the respective two groups are binding.

In the general formula (I), examples of the halogen atom represented by $R^1$ to $R^{16}$ may include fluorine, chlorine, bromine, iodine and the like.

In the general formula (I), examples of the alkyl group having 1 to 20 carbon atoms optionally having substituents represented by $R^1$ to $R^{16}$ may include unsubstituted alkyl groups having 1 to 20 carbon atoms such as methyl, ethyl, n-propyl, isopropyl, n-butyl, isobutyl, sec-butyl, tert-butyl, n-pentyl, isopentyl, neopentyl, tert-amyl, 1,2-dimethylpropyl, n-hexyl, cyclohexyl, 1,3-dimethylbutyl, 1-isopropylpropyl, 1,2-dimethylbutyl, n-heptyl, 2-heptyl, 1,4-dimethylpentyl, tert-heptyl, 2-methyl-1-isopropylpropyl, 1-ethyl-3-methylbutyl, n-octyl, tert-octyl, 2-ethylhexyl, 2-methylhexyl, 2-propylhexyl, n-nonyl, isononyl, n-decyl, isodecyl, n-undecyl, isoundecyl, n-dodecyl, isododecyl, n-tridecyl, isotridecyl, n-tetradecyl, isotetradecyl, n-pentadecyl, isopentadecyl, n-hexadecyl, isohexadecyl, n-heptadecyl, isoheptadecyl, n-octadecyl, isooctadecyl, n-nonadecyl, isononadecyl, n-icosyl, isoicosyl and the like. Examples of the alkyl groups having 1 to 20 carbon atoms having substituents may include groups formed by substituting the above-mentioned alkyl groups with the substituents mentioned below.

Furthermore, in the general formula (I), examples of the alkoxy group having 1 to 20 carbon atoms optionally having substituents represented by $R^1$ to $R^{16}$ may include groups corresponding to the above-mentioned alkyl groups, and specific examples may include unsubstituted alkoxy groups having 1 to 20 carbon atoms such as methoxy, ethoxy, n-propoxy, isopropoxy, n-butoxy, isobutoxy, sec-butoxy, tert-butoxy, n-pentyloxy, isopentyloxy, neopentyloxy, 1,2-dimethyl-propoxy, n-hexyloxy, cyclohexyloxy, 1,3-dimethylbutoxy and 1-isopropylpropoxy. Examples of the alkoxy groups having 1 to 20 carbon atoms having substituents may include groups formed by substituting the above-mentioned alkoxy group with the substituents mentioned below.

Furthermore, in the above-mentioned general formula (I), examples of the aryl group having 6 to 20 carbon atoms optionally having substituents represented by $R^1$ to $R^{16}$ may include unsubstituted aryl groups having 6 to 20 carbon atoms such as phenyl, naphthyl, anthracen-1-yl and phenanthren-1-yl. Examples of the aryl groups having 6 to 20 carbon atoms having substituents may include groups formed by substituting the above-mentioned aryl groups with the substituents mentioned below.

Furthermore, in the above-mentioned general formula (I), examples of the aryloxy group having 6 to 20 carbon atoms optionally having substituents represented by $R^1$ to $R^{16}$ may include groups corresponding to the above-mentioned aryl groups, and specific examples may include unsubstituted aryloxy groups having 6 to 20 carbon atoms such as phenoxy and naphthoxy. Examples of the aryloxy groups having 1 to 20 carbon atoms having substituents may include groups formed by substituting the above-mentioned aryloxy groups with the substituents mentioned below.

Furthermore, in the above-mentioned general formula (I), examples of the arylalkyl group having 7 to 20 carbon atoms optionally having substituents represented by $R^1$ to $R^{16}$ may include unsubstituted arylalkyl groups having 7 to 20 carbon atoms such as benzyl, phenethyl, 2-phenylpropan-2-yl, styryl, cinnamyl, diphenylmethyl and triphenylmethyl. Examples of the arylalkyl groups having 7 to 20 carbon atoms having substituents may include groups formed by substituting the above-mentioned arylalkyl groups with the substituents mentioned below.

Furthermore, in the above-mentioned general formula (I), examples of the cycloalkyl group having 5 to 12 carbon atoms optionally having substituents represented by $R^1$ to $R^{16}$ may include unsubstituted cycloalkyl groups having 5 to 12 carbon atoms such as cyclopentyl, cyclohexyl, cyclooctyl, cyclododecyl and 4-methylcyclohexyl. Examples of the cycloalkyl groups having 5 to 12 carbon atoms having substituents may include groups formed by substituting the above-mentioned cycloalkyl groups with the substituents mentioned below.

Furthermore, in the above-mentioned general formula (I), examples of the alkylthio group having 1 to 20 carbon atoms optionally having substituents represented by $R^1$ to $R^{16}$ may include unsubstituted alkylthio groups having 1 to 20 carbon atoms such as methylthio, ethylthio, n-propylthio, iso-propylthio, n-butylthio, iso-butylthio, sec-butylthio, t-butylthio, n-pentylthio, iso-pentylthio, neo-pentylthio, 1,2-dimethylpropylthio, n-hexylthio, cyclohexylthio, n-heptylthio, 2-ethylhexylthio, n-octylthio and n-nonylthio. Examples of the alkylthio groups having 1 to 20 carbon atoms having substituents may include groups formed by substituting the above-mentioned alkylthio groups with the substituents mentioned below, and specific examples may include methoxyethylthio, ethoxyethylthio, propoxyethylthio, butoxyethylthio, aminoethylthio, n-butylaminoethylthio, benzylaminoethylthio, methylcarbonylaminoethylthio, phenylcarbonylaminoethylthio, methylsulfonylaminoethylthio, phenylsulfonylaminoethylthio, dimethylaminoethylthio, diethylaminoethylthio and the like.

Furthermore, in the above-mentioned general formula (I), examples of the arylthio group having 6 to 20 carbon atoms optionally having substituents represented by $R^1$ to $R^{16}$ may include phenylthio, naphthylthio and the like. Examples of the arylthio groups having 6 to 20 carbon atoms having substituents may include groups formed by substituting the above-mentioned arylthio groups with the substituents mentioned below, and specific examples may include 4-methylphenylthio, 4-ethylphenylthio, 4-propylphenylthio, 4-t-butylphenylthio, 4-methoxyphenylthio, 4-ethoxyphenylthio, 4-aminophenylthio, 4-alkylaminophenylthio, 4-dialkylaminophenylthio, 4-phenylaminophenylthio, 4-diphenylaminophenylthio, 4-hydroxyphenylthio, 4-chlorophenylthio, 4-bromophenylthio, 2-methylphenylthio, 2-ethylphenylthio, 2-propylphenylthio, 2-t-butylphenylthio, 2-methoxyphenylthio, 2-ethoxyphenylthio, 2-aminophenylthio, 2-alkylaminophenylthio, 2-dialkylaminophenylthio, 2-phenylaminophenylthio, 2-diphenylaminophenylthio, 2-hydroxyphenylthio, 4-dimethylaminophenylthio, 4-methylaminophenylthio, 4-methylcarbonylaminophenylthio, 4-phenylcarbonylaminophenylthio, 4-methylsulfonylaminophenylthio, 4-phenylsulfonylaminophenylthio and the like.

Furthermore, examples of the alkylamino group having 1 to 20 carbon atoms optionally having substituents represented by $R^1$ to $R^{16}$ may include unsubstituted alkylamino groups having 1 to 20 carbon atoms such as methylamino, ethylamino, n-propylamino, iso-propylamino, butylamino, pentylamino, dipentylamino, hexylamino, heptylamino, octylamino, 2-ethylhexylamino, nonylamino, benzylamino, dimethylamino, diethylamino, di-n-propylamino, di-iso-propylamino, dibutylamino, dipentylamino, dihexylamino, diheptylamino, dioctylamino, di-2-ethylhexylamino, dinonylamino, methylethylamino and the like. Examples of the alkylamino groups having 1 to 20 carbon atoms having substituents may include groups formed by substituting the above-mentioned alkylamino groups with the substituents mentioned below.

Furthermore, in the above-mentioned general formula (I), examples of the arylamino group having 6 to 20 carbon atoms optionally having substituents represented by $R^1$ to $R^{16}$ may include unsubstituted arylamino groups having 6 to 20 carbon atoms such as phenylamino, naphthylamino and diphenylamino. Examples of the arylamino groups having 6 to 20 carbon atoms having substituents may include groups formed by substituting the above-mentioned arylamino groups with the substituents mentioned below, and specific examples may include 4-methylphenylamino, 4-methoxyphenylamino, hydroxyphenylamino and the like.

Furthermore, in the above-mentioned general formula (I), the adjacent two groups of the groups represented by $R^1$ to $R^{16}$ may link to form a 5-membered ring or a 6-membered ring together with the carbon atom to which the respective two groups are binding. The 5-membered ring or 6-membered ring may have substituents. Examples of such 5-membered ring may include a cyclopentene ring, a cyclopentadiene ring, an imidazole ring, a thiazole ring, a pyrrazole ring, an oxazole ring, an isoxazole ring, a thiophene ring, a furan ring, a pyrrole ring and the like, and examples of the 6-membered ring may include a cyclohexane ring, a cyclohexene ring, a cyclohexadiene ring, a benzene ring, a pyrizine ring, a piperazine ring, a piperidine ring, a morpholine ring, a pyrazine ring, a pyron ring, a pyrrolidine ring and the like.

Furthermore, in the above-mentioned general formula (I), examples of the substituents for the alkyl group having 1 to 20 carbon atoms optionally having substituents, alkoxy group having 1 to 20 carbon atoms optionally having substituents, aryl group having 6 to 20 carbon atoms optionally having substituents, aryloxy group having 6 to 20 carbon atoms optionally having substituents, arylalkyl group having 7 to 20 carbon atoms optionally having substituents, cycloalkyl group having 5 to 12 carbon atoms optionally having substituents, alkylthio group having 1 to 20 carbon atoms optionally having substituents, alkylamino group having 1 to 20 carbon atoms optionally having substituents and arylamino group having 6 to 20 carbon atoms optionally having substituents, which are represented by $R^1$ to $R^{16}$, and for the 5-membered ring or 6-membered ring optionally having substituents, which is formed by the connection of the adjacent two groups among the groups represented by the above-mentioned $R^1$ to $R^{16}$, may include the following substituents. In the case when $R^1$ to $R^{16}$ are the above-mentioned groups containing carbon atoms and those groups have substituents containing carbon atoms among the following substituents, the numbers of the carbon atoms of the entirety of $R^1$ to $R^{16}$ including the substituents shall satisfy the prescribed scopes.

Examples of the substituents may include alkyl groups such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl and decyl;

alkoxy groups such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy and decyloxy;
  alkylthio groups such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio and 2-ethylhexylthio;
  alkenyl groups such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl and tricosenyl;
  arylalkyl groups such as benzyl, phenethyl, diphenylmethyl, triphenylmethyl, styryl and cinnamyl;
  aryl groups such as phenyl and naphthyl;
  aryloxy groups such as phenoxy and naphthyloxy;
  arylthio groups such as phenylthio and naphthylthio;
  heterocyclic groups such as pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl and 2,4-dioxyoxazolidin-3-yl;
  halogen atoms such as fluorine, chlorine, bromine and iodine;
  acyl groups such as acetyl, 2-chloroacetyl, propionyl, octanoyl, acryloyl, methacryloyl, phenylcarbonyl(benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl and carbamoyl;
  acyloxy groups such as acetyloxy and benzoyloxy;
  substituted amino groups such as amino, ethylamino, dimethylamino, diethylamino, butylamino, cyclopentylamino, 2-ethylhexylamino, dodecylamino, anilino, chlorophenylamino, toluidino, anisidino, N-methylanilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methylmethoxycarbonylamino, phenoxycarbonylamino, sulfamoylamino, N,N-dimethylaminosulfonylamino, methylsulfonylamino, butylsulfonylamino and phenylsulfonylamino;
  a sulfonamide group, a sulfonyl group, a carboxyl group, a cyano group, a sulfo group, a hydroxyl group, a nitro group, a mercapto group, an imide group, a carbamoyl group, a sulfonamide group, and the like,
  and these groups may further be substituted. Furthermore, the carboxyl group and sulfo group may form salts.

$R^1$ to $R^{16}$ in the above-mentioned general formula (I) are each preferably a hydrogen atom or an alkyl group, more preferably, a hydrogen atom or a methyl group, and even more preferably a hydrogen atom, from the viewpoint of near-infrared absorbability.

Specific examples of the novel compound represented by the above-mentioned general formula (I) of the present invention may include the following Compounds No. 1 to No. 14, but are not limited to these compounds.

[Chemical Formula 3]

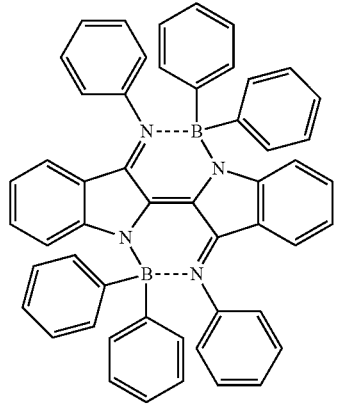

Compound No. 1

Compound No. 2

[Chemical Formula 4]
Compound No. 3
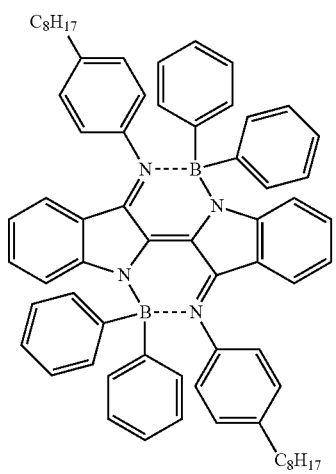
Compound No. 4
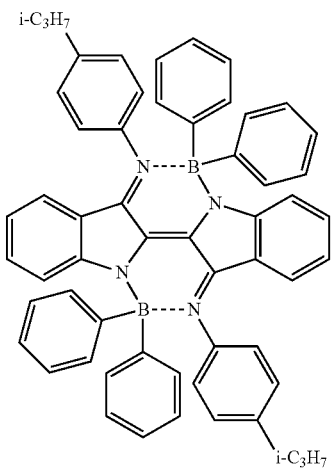
[Chemical Formula 5]
Compound No. 5
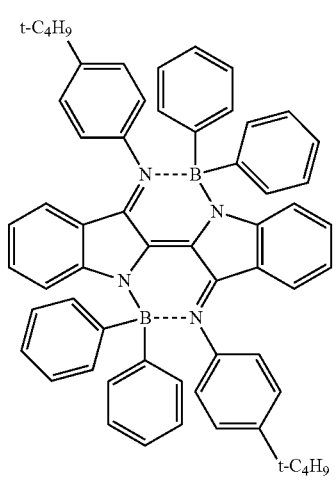
Compound No. 6
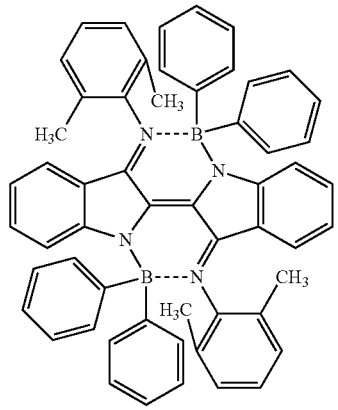
[Chemical Formula 6]
Compound No. 7
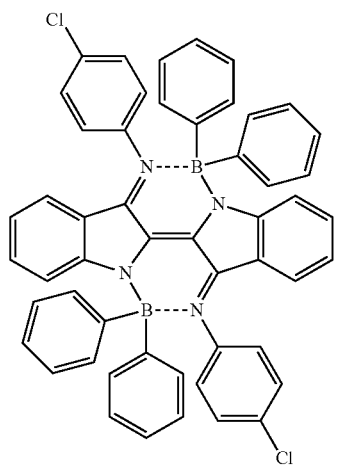
Compound No. 8
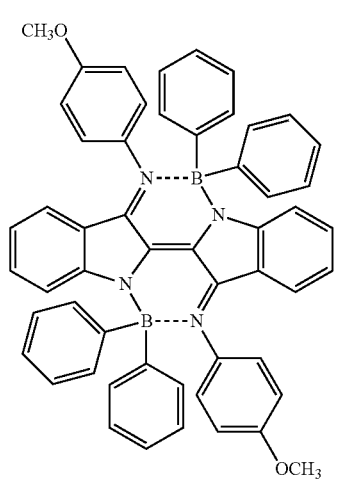

[Chemical Formula 7]
Compound No. 9
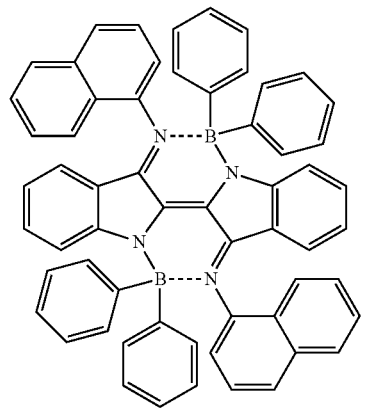
Compound No. 10
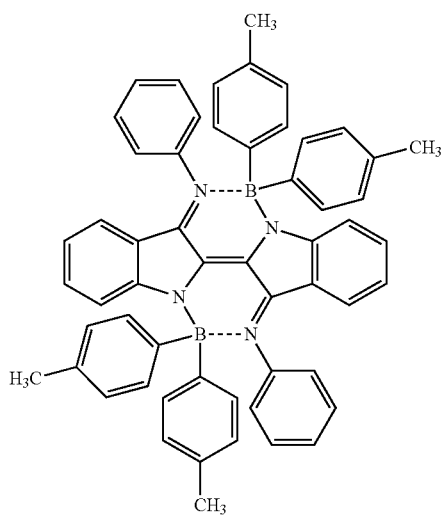
[Chemical Formula 8]
Compound No. 11
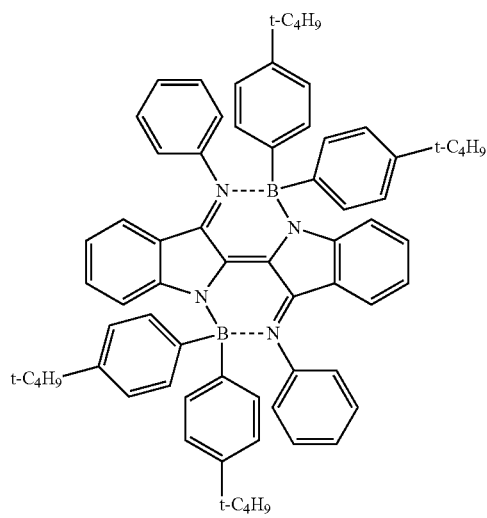
Compound No. 12
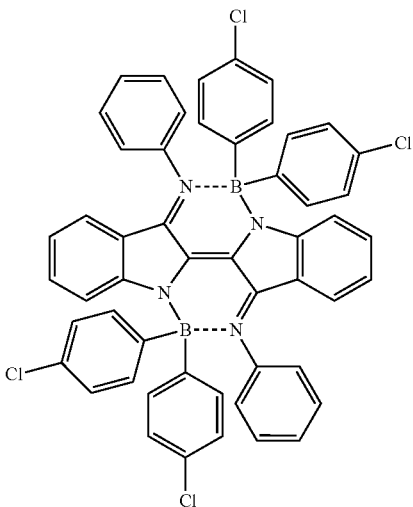
[Chemical Formula 9]
Compound No. 13
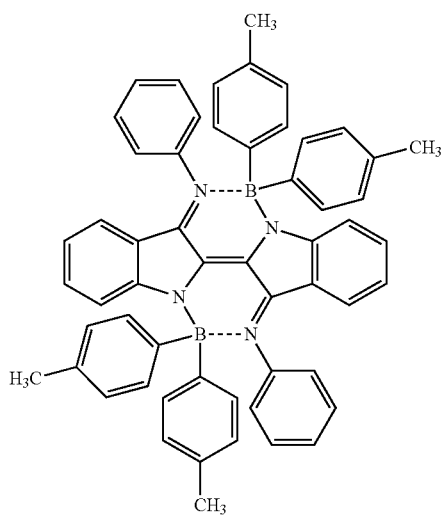
Compound No. 14
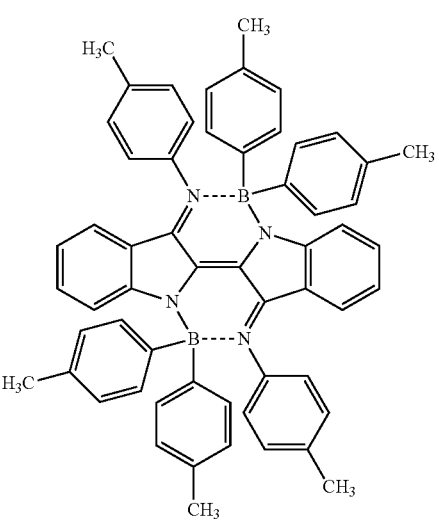

Next, the method for synthesizing the boron compound represented by the above-mentioned general formula (I) of the present invention will be explained.

First, a step of obtaining an intermediate from a compound having an indigo skeleton as a raw material will be explained. In this step, the compound having an indigo skeleton and a compound having an aniline skeleton are reacted in a solvent in the presence of titanium tetrachloride and 1,4-diazabicyclo[2.2.2]octane (DABCO) to give an intermediate. For example, a scheme in the case when Intermediate-1 for the synthesis of the above-mentioned Compound No. 1 using indigo as a raw material is as shown in the following Scheme 1.

[Chemical Formula 10]

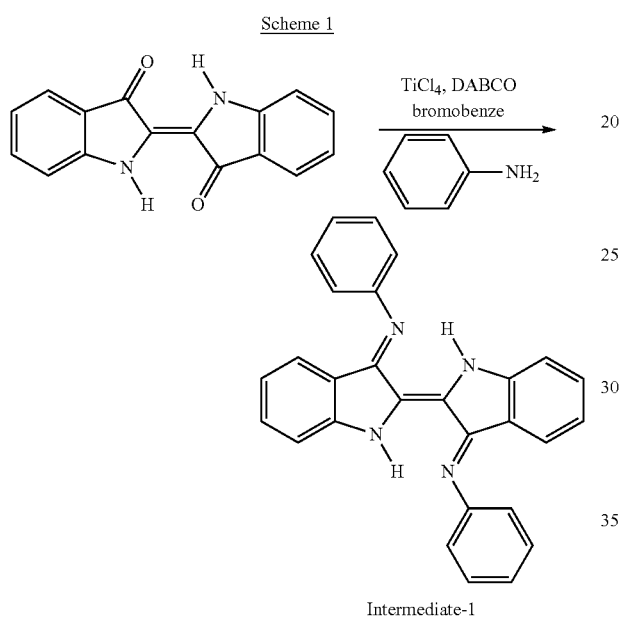

Intermediate-1

Although the reaction solvent used for obtaining the intermediate is not specifically limited as long as titanium tetrachloride and DABCO are not inactivated, a solvent that dissolves the compound having an indigo skeleton is preferable, and specific examples may include aromatic-based solvents (toluene, xylene, chlorobenzene, nitrobenzene, mesitylene, p-cymene, dichlorobenzene, Solvent Naphtha), aliphatic-based high-boiling point solvents (decane and the like) and the like. Toluene, xylene, chlorobenzene, orthodichlorobenzene, mesitylene and bromobenzene are preferable, and bromobenzene is more preferable.

Although the reaction temperature is not specifically limited, a temperature that is required for dissolving the compound having an indigo skeleton as a raw material is preferable, and it is preferable to react at a temperature at which the used solvent is refluxed. From these viewpoints, a range of 100° C. to 200° C. is preferable, and 130° C. to 180° C. is more preferable.

The reaction time is not specifically limited, and the reaction may be conducted by confirming the progress of the reaction by HPLC or TLC until the reaction is completed. After the completion of the reaction, post-treatments such as an extraction treatment, a purification treatment and the like may be conducted.

The use amount of the compound having an aniline skeleton used is required to be 2 mol or more with respect to 1 mol of the compound having an indigo skeleton, and is preferably 3 to 4 mol.

Furthermore, the use amount of the titanium tetrachloride used is preferably 2 to 3 mol with respect to 1 mol of the compound having an indigo skeleton.

Furthermore, the use amount of the DABCO used is preferably 8 to 12 mol with respect to 1 mol of the compound having an indigo skeleton.

Next, a step of obtaining the boron compound represented by the above-mentioned general formula (I) of the present invention from the intermediate will be explained. In this step, the intermediate obtained in the above-mentioned step is reacted with a boron compound such as a borinic acid ester in a solvent in the presence of a Lewis acid such as titanium tetrachloride to give the boron compound of the present invention. For example, a scheme for obtaining Compound No. 1, which is the boron compound of the present invention, from Intermediate-1 obtained in the above-mentioned Scheme 1 is as shown in the following Scheme 2.

[Chemical Formula 11]

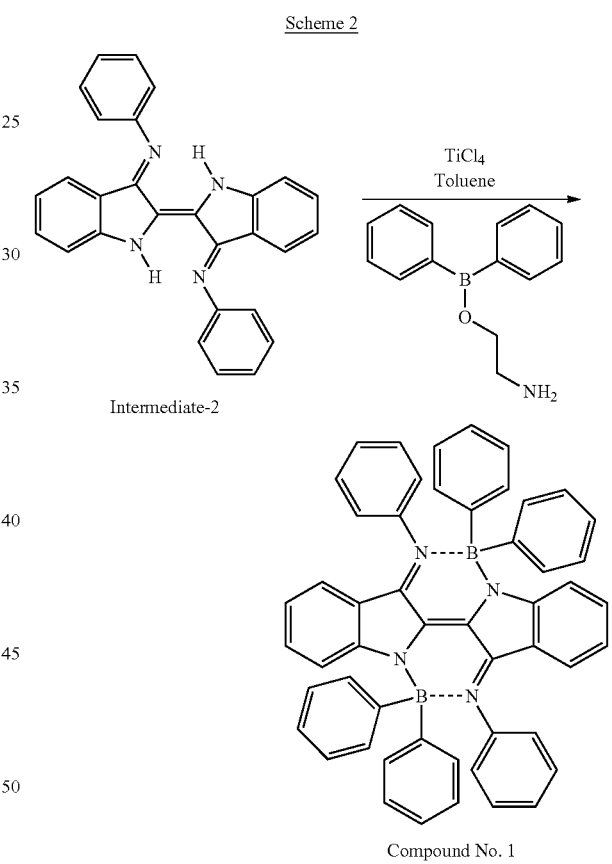

Compound No. 1

Although the reaction solvent used for obtaining the boron compound represented by the above-mentioned general formula (I) from the intermediate is not specifically limited as long as it is a reaction solvent that does not inactivate the Lewis acid such as titanium tetrachloride, a reaction solvent that dissolves the intermediate is preferable, and specific examples may include aromatic-based solvents (toluene, xylene, chlorobenzene, nitrobenzene, mesitylene, p-cymene, dichlorobenzene, Solvent Naphtha), aliphatic-based high-boiling point solvents (decane and the like) and the like. Toluene, xylene, chlorobenzene, orthodichlorobenzene, mesitylene and bromobenzene are preferable, and toluene is more preferable.

Although the reaction temperature is not specifically limited, a temperature that is required for dissolving the intermediate is preferable, and it is preferable to react at a temperature at which the used solvent is refluxed. From these viewpoints, a range of 50° C. to 170° C. is preferable, 70° C. to 150° C. is more preferable, and 90° C. to 130° C. is even more preferable.

The reaction time is not specifically limited, and the reaction may be conducted by confirming the progress of the reaction by HPLC or TLC until the reaction is completed. After the completion of the reaction, post-treatments such as a treatment to inactivate the used Lewis acid, an extraction treatment, and purification treatments such as a crystallization treatment may be conducted.

As the boron compound used, a borinic acid ester is preferable, and 2-aminoethyl diphenylborinate is specifically preferable. The use amount of the boron compound used is 2 mol or more, preferably 2.0 to 2.2 mol, with respect to 1 mol of the intermediate.

Although the Lewis acid used is not specifically limited, titanium tetrachloride, aluminum chloride, iron chloride, zinc chloride, tin chloride, boron trifluoride, and bromides thereof are preferable, titanium chloride, boron trifluoride and aluminum chloride are more preferable, and titanium tetrachloride is even more preferable. The use amount of the Lewis acid used is preferably 1 to 4.4 mol with respect to 1 mol of the intermediate.

The boron compound represented by the above-mentioned general formula (I) of the present invention explained above has absorption in the near-infrared ray range and low absorption in the visible ray range, and thus can be preferably used as a near-infrared absorber.

Although the light absorption property of the boron compound represented by the above-mentioned general formula (I) is not specifically limited, when use as a near-infrared absorber is taken into consideration, it is preferable that the boron compound has a maximum absorption at 700 to 1,050 nm, specifically at 700 to 1,000 nm. Furthermore, it is preferable to selectively absorb near-infrared ray at a wavelength of 700 to 1,000 nm. Furthermore, it is preferable that the boron compound has lower absorption in the visible ray range.

Next, the near-infrared absorber, near-infrared absorbing synthetic resin composition and near-infrared absorbing material of the present invention will be explained.

The near-infrared absorber of the present invention contains the above-mentioned boron compound represented by the general formula (I) of the present invention, and may be the boron compound represented by the above-mentioned general formula (I) of the present invention itself, or may suitably contain optional additives that can be used in the near-infrared absorbing synthetic resin composition of the present invention, and the components other than the boron compound of the present invention are not specifically limited.

The near-infrared absorber of the present invention (the boron compound represented by the above-mentioned general formula (I) of the present invention) has low absorption in the visible ray range, and even when this is used in a synthetic resin, the transparency of the resin is not damaged, and the inherent color of the resin is not affected, and thus it is preferable to use the synthetic resin as a near-infrared absorbing synthetic resin composition. Furthermore, since the near-infrared absorber is excellent in heat-resistance, it is also preferable to use as a near-infrared absorbing thermoplastic resin composition in which the near-infrared absorber is incorporated in a thermoplastic resin as a kneading-type near-infrared absorber.

The content of the boron compound represented by the above-mentioned general formula (I) in the near-infrared absorber of the present invention is not specifically limited, and in the case when it is used in a synthetic resin, it is preferably in the range of the content of the boron compound represented by the above-mentioned general formula (I) in the near-infrared absorbing synthetic resin composition mentioned below.

The near-infrared absorbing synthetic resin composition of the present invention contains the near-infrared absorber of the present invention (the boron compound represented by the above-mentioned general formula (1)) in a synthetic resin.

Examples of the synthetic resin that can be used in the present invention may include thermoplastic resins, thermosetting resins, fluorine-based resins, silicone resins and the like.

Examples of the above-mentioned thermoplastic resins may include thermoplastic resins such as α-olefin polymers such as polypropylenes, high density polyethylenes, low density polyethylenes, straight chain low density polyethylenes, crosslinked polyethylenes, ultrahigh molecular weight polyethylenes, polybutene-1, poly-3-methylpentene and poly-4-methylpentene or polyolefin-based resins such as ethylene-vinyl acetate copolymers, ethylene-ethyl acrylate copolymers and ethylene-propylene copolymers, and copolymers thereof; halogen-containing resins such as polyvinyl chloride, polyvinylidene chloride, polyethylene chloride, polypropylene chloride, polyvinylidene fluoride, chlorinated rubbers, vinyl chloride-vinyl acetate copolymers, vinyl chloride-ethylene copolymers, vinyl chloride-vinylidene chloride copolymers, vinyl chloride-vinylidene chloride-vinyl acetate tercopolymers, vinyl chloride-acrylic acid ester copolymers, vinyl chloride-maleic acid ester copolymers and vinyl chloride-cyclohexylmaleimide copolymers; petroleum resins, coumarone resins, polystyrenes, polyvinyl acetate, acrylic resins, copolymers of styrene and/or α-methylstyrene with other monomers (for example, maleic anhydride, phenylmaleimide, methyl methacrylate, butadiene, acrylonitrile and the like) (for example, AS resins, ABS resins, ACS resins, SBS resins, MBS resins, heat-resistant ABS resins and the like); polymethyl methacrylate, polyvinyl alcohol, polyvinyl formal, polyvinyl butyral; polyalkylene telephthalates such as polyethylene telephthalate, polybutylene telephthalate and polycyclohexanedimethylene telephthalate, aromatic polyesters such as polyalkylene naphthalates such as polyethylene naphthalate and polybutylene naphthalate, and straight chain polyesters such as polytetramethylene telephthalate; degradable aliphatic polyesters such as polyhydroxy butyrate, polycaprolactone, polybutylene succinate, polyethylene succinate, polylactic acid, polymalic acid, polyglycolic acid, polydioxane and poly(2-oxetanone); polyphenylene oxide, polyamides such as polycaprolactam and polyhexamethylene adipamide, polycarbonates, polycarbonate/ABS resins, branched polycarbonates, polyacetals, polyphenylene sulfides, polyurethanes, cellulose-based resins and polyimide resins, and blends thereof.

Furthermore, the above-mentioned thermoplastic resins may be elastomers such as isoprene rubbers, butadiene rubbers, acrylonitrile-butadiene copolymerized rubbers, styrene-butadiene copolymerized rubbers, fluorine rubbers, silicone rubbers, olefin-based elastomers, styrene-based elastomers, polyester-based elastomers, nitrile-based elastomers, nylon-based elastomers, vinyl chloride-based elastomers, polyamide-based elastomers and polyurethane-based elastomers.

Examples of the above-mentioned thermosetting resins may include phenolic resins, urea resins, melamine resins, epoxy resins, unsaturated polyester resins and the like.

Examples of the above-mentioned fluorine resins may include polytetrafluoroethylene, polyvinylidene fluoride, polychlorotrifluoroethylene, polyvinyl fluoride, perfluoroalkoxyfluorine resins, tetrafluoroethylene-ethylene copolymers and the like.

Examples of the above-mentioned silicone resins may include dimethylsilicone resins, methylphenylsilicone resins, methylvinylsilicone resins, epoxy-modified silicone resins, acrylic-modified silicone resins and the like.

Furthermore, examples of the synthetic resins may include silicone rubber polyethersulfones, polysulfones, polyphenylene ethers, polyether ketones, polyether ether ketones, liquid crystal polymers and the like.

In the present invention, these synthetic resins may be used alone, or two or more kinds may be used. Furthermore, the synthetic resins may be in the form of an alloy.

These synthetic resins can be used irrespective of the molecular weight, the polymerization degree, the density, the softening point, the ratio of insoluble components in a solvent, the degree of steric regularity, the presence or absence of a catalyst residue, the kinds and incorporation ratio of monomers as raw materials, the kind of a polymerization catalyst (for example, a Ziegler catalyst, a metallocene catalyst and the like), and the like.

Among the above-mentioned synthetic resins, thermoplastic resins are preferable from the viewpoints of the compatibility and processability of the boron compound represented by the above-mentioned general formula (I), and among the thermoplastic resins, polycarbonates and polymethyl methacrylate are specifically preferable from the viewpoints of transparency and near-infrared absorbability.

In the near-infrared absorbing synthetic resin composition of the present invention, the content of the boron compound represented by the above-mentioned general formula (I) is preferably 0.001 to 20 parts by mass, more preferably 0.01 to 10 parts by mass, even more preferably 0.1 to 5 parts by mass, with respect to 100 parts by mass of the above-mentioned synthetic resin. When the content of the boron compound of the general formula (I) is lower than 0.001 parts by mass, it is possible that a sufficient near-infrared absorbability cannot be achieved, whereas when the content goes beyond 20 parts by mass, it is not cost efficient since an effect that is worth the use amount cannot be obtained, and it is also possible that the transparency in the visible region is impaired.

The method for incorporating the boron compound represented by the above-mentioned general formula (I) into the synthetic resin may follow a conventional method, and is not specifically limited. For example, in the case when a thermoplastic resin is used as the synthetic resin, any method that is generally used in the cases when various additives are added to a thermoplastic resin can be used, and for example, the thermoplastic resin may be incorporated by mixing and kneading by roll kneading, bumper kneading, an extruder, a kneader or the like.

Alternatively, a solution of the near-infrared absorbing synthetic resin composition may be formulated and used by dissolving or dispersing the above-mentioned boron compound represented by the general formula (I) and the above-mentioned synthetic resin in various solvents.

Where necessary, additives used in synthetic resins such as phenol-based antioxidants, phosphorus-based antioxidants, thioether-based antioxidants, ultraviolet absorbers and hindered amine-based light stabilizers may be incorporated in the near-infrared absorbing synthetic resin composition of the present invention to thereby stabilize the composition.

Examples of the above-mentioned phenol-based antioxidants may include 2,6-di-tert-butyl-p-cresol, 2,6-diphenyl-4-octadecyloxyphenol, distearyl (3,5-di-tert-butyl-4-hydroxybenzyl)phosphonate, 1,6-hexamethylenebis[(3,5-di-tert-butyl-4-hydroxyphenyl)propionic acid amide], 4,4'-thiobis (6-tert-butyl-m-cresol), 2,2'-methylenebis(4-methyl-6-tert-butylphenol), 2,2'-methylenebis(4-ethyl-6-tert-butylphenol), 4,4'-butylidenebis(6-tert-butyl-m-cresol), 2,2'-ethylidenebis (4,6-di-tert-butylphenol), 2,2'-ethylidenebis(4-sec-butyl-6-tert-butylphenol), 1,1,3-tris(2-methyl-4-hydroxy-5-tert-butylphenyl)butane, 1,3,5-tris(2,6-dimethyl-3-hydroxy-4-tert-butylbenzyl)isocyanurate, 1,3,5-tris(3,5-di-tert-butyl-4-hydroxybenzyl)isocyanurate, 1,3,5-tris(3,5-di-tert-butyl-4-hydroxybenzyl)-2,4,6-trimethylbenzene, 2-tert-butyl-4-methyl-6-(2-acryloyloxy-3-tert-butyl-5-methylbenzyl) phenol, stearyl (3,5-di-tert-butyl-4-hydroxyphenyl) propionate, tetrakis[methyl 3-(3,5-di-tert-butyl-4-hydroxyphenyl)propionate]methane, thiodiethylene glycol bis[(3,5-di-tert-butyl-4-hydroxyphenyl)propionate], 1,6-hexamethylenebis[(3,5-di-tert-butyl-4-hydroxyphenyl)propionate], bis[3,3-bis(4-hydroxy-3-tert-butylphenyl)butylic acid]glycol ester, bis[2-tert-butyl-4-methyl-6-(2-hydroxy-3-tert-butyl-5-methylbenzyl)phenyl]telephthalate, 1,3,5-tris[(3,5-di-tert-butyl-4-hydroxyphenyl)propionyloxyethyl]isocyanurate, 3,9-bis[1,1-dimethyl-2-{(3-tert-butyl-4-hydroxy-5-methylphenyl)propionyloxy}ethyl]-2,4,8,10-tetraoxaspiro [5,5]undecane, triethylene glycol bis[(3-tert-butyl-4-hydroxy-5-methylphenyl)propionate] and the like.

The content of the above-mentioned phenol-based antioxidant is preferably 0.001 to 10 parts by mass, more preferably 0.05 to 5 parts by mass with respect to 100 parts by mass of the synthetic resin.

Examples of the above-mentioned phosphorus-based antioxidant may include trisnonylphenyl phosphite, tris[2-tert-butyl-4-(3-tert-butyl-4-hydroxy-5-methylphenylthio)-5-methylphenyl]phosphite, tridecyl phosphite, octyl diphenyl phosphite, di(decyl)monophenyl phosphite, di(tridecyl)pentaerythritol diphosphite, di(nonylphenyl)pentaerythritol diphosphite, bis(2,4-di-tert-butylphenyl)pentaerythritol diphosphite, bis(2,6-di-tert-butyl-4-methylphenyl)pentaerythritol diphosphite, bis(2,4,6-tri-tert-butylphenyl)pentaerythritol diphosphite, bis(2,4-dicumylphenyl)pentaerythritol diphosphite, tetra(tridecyl)isopropylidenediphenol diphosphite, tetra(tridecyl)-4,4'-n-butylidenebis(2-tert-butyl-5-methylphenol)diphosphite, hexa(tridecyl)-1,1,3-tris(2-methyl-4-hydroxy-5-tert-butylphenyl)butanetriphosphite, tetrakis(2,4-di-tert-butylphenyl)biphenylenediphosphonite, 9,10-dihydro-9-oxa-10-phosphaphenanthrene-10-oxide, 2,2'-methylenebis(4,6-tert-butylphenyl)-2-ethylhexyl phosphite, 2,2'-methylenebis(4,6-tert-butylphenyl)-octadecyl phosphite, 2,2'-ethylidenebis(4,6-di-tert-butylphenyl)fluorophosphite, tris(2-[(2,4,8,10-tetrakistert-butyldibenzo[d,f][1,3,2]dioxaphosphepin-6-yl)oxy]ethyl)amine, phosphites of 2-ethyl-2-butylpropylene glycol and 2,4,6-tri-tert-butylphenol, and the like.

The content of the above-mentioned phosphorus-based antioxidant is preferably 0.001 to 10 parts by mass, more preferably 0.05 to 5 parts by mass, with respect to 100 parts by mass of the synthetic resin.

Examples of the above-mentioned thioether-based antioxidants may include dialkyl thiodipropionates such as dilauryl thiodipropionate, dimyristyl thiodipropionate and distearyl thiodipropionate, and pentaerythritol tetra(β-alkylthiopropionic acid esters.

The content of the above-mentioned thioether-based antioxidant is preferably 0.001 to 10 parts by mass, more preferably 0.05 to 5 parts by mass, with respect to 100 parts by mass of the synthetic resin.

Examples of the above-mentioned ultraviolet absorber may include 2-hydroxybenzophenones such as 2,4-dihydroxybenzophenone, 2-hydroxy-4-methoxybenzophenone, 2-hydroxy-4-octoxybenzophenone and 5,5'-methylenebis(2-hydroxy-4-methoxybenzophenone); 2-(2'-hydroxyphenyl)benzotriazoles such as 2-(2'-hydroxy-5'-methylphenyl)benzotriazole, 2-(2'-hydroxy-3',5'-di-tert-butylphenyl)-5-chlorobenzotriazole, 2-(2'-hydroxy-3'-tert-butyl-5'-methylphenyl)-5-chlorobenzotriazole, 2-(2'-hydroxy-5'-tert-octylphenyl)benzotriazole, 2-(2'-hydroxy-3',5'-dicumylphenyl)benzotriazole, 2,2'-methylenebis(4-tert-octyl-6-(benzotriazolyl)phenol) and 2-(2'-hydroxy-3'-tert-butyl-5'-carboxyphenyl)benzotriazole; benzoates such as phenyl salicylate, resorcinol monobenzoate, 2,4-di-tert-butylphenyl-3,5-di-tert-butyl-4-hydroxybenzoate, 2,4-di-tert-amylphenyl-3,5-di-tert-butyl-4-hydroxybenzoate and hexadecyl-3,5-di-tert-butyl-4-hydroxybenzoate; substituted oxanilides such as 2-ethyl-2'-ethoxyoxanilide and 2-ethoxy-4'-dodecyloxanilide; cyanoacrylates such as ethyl-α-cyano-β,β-diphenylacrylate and methyl-2-cyano-3-methyl-3-(p-methoxyphenyl)acrylate; triaryltriazines such as 2-(2-hydroxy-4-octoxyphenyl)-4,6-bis(2,4-di-tert-butylphenyl)-s-triazine, 2-(2-hydroxy-4-methoxyphenyl)-4,6-diphenyl-s-triazine and 2-(2-hydroxy-4-propoxy-5-methylphenyl)-4,6-bis(2,4-di-tert-butylphenyl)-s-triazine.

The content of the above-mentioned ultraviolet absorber is preferably 0.001 to 30 parts by mass, more preferably 0.05 to 10 parts by mass with respect to 100 parts by mass of the synthetic resin.

Examples of the above-mentioned hindered amine-based light stabilizers may include hindered amine compounds such as 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl)sebacate, bis(1,2,2,6,6-tetramethyl-4-piperidyl) sebacate, bis(1-octoxy-2,2,6,6-tetramethyl-4-piperidyl)sebacate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, bis(2,2,6,6-tetramethyl-4-piperidyl)-di(tridecyl)-1,2,3,4-butanetetracarboxylate, bis(1,2,2,6,6-pentamethyl-4-piperidyl)-di(tridecyl)-1,2,3,4-butanetetracarboxylate, bis(1,2,2,4,4-pentamethyl-4-piperidyl)-2-butyl-2-(3,5-di-tert-butyl-4-hydroxybenzyl)malonate, 1-(2-hydroxyethyl)-2,2,6,6-tetramethyl-4-piperidinol/diethyl succinate polycondensate, 1,6-bis(2,2,6,6-tetramethyl-4-piperidylamino)hexane/2,4-dichloro-6-morpholino-s-triazine polycondensate, 1,6-bis(2,2,6,6-tetramethyl-4-piperidylamino)hexane/2,4-dichloro-6-tert-octylamino-s-triazine polycondensate, 1,5,8,12-tetrakis[2,4-bis(N-butyl-N-(2,2,6,6-tetramethyl-4-piperidyl)amino)-s-triazin-6-yl]-1,5,8,12-tetraazadodecane, 1,5,8,12-tetrakis[2,4-bis(N-butyl-N-(1,2,2,6,6-pentamethyl-4-piperidyl)amino)-s-triazin-6-yl]-1,5,8,12-tetraazadodecane, 1,6,11-tris[2,4-bis(N-butyl-N-(2,2,6,6-tetramethyl-4-piperidyl)amino)-s-triazin-6-yl]aminoundecane and 1,6,11-tris[2,4-bis(N-butyl-N-(1,2,2,6,6-pentamethyl-4-piperidyl)amino)-s-triazin-6-yl]aminoundecane.

The content of the above-mentioned hindered amine-based light stabilizer is preferably 0.001 to 30 parts by mass, more preferably 0.05 to 10 parts by mass with respect to 100 parts by mass of the synthetic resin.

Furthermore, where necessary, additives that are generally incorporated in synthetic resins such as nucleating agents such as aluminum p-tert-butylbenzoate, metal salts of aromatic phosphate esters and dibenzylidene sorbitol, antistatic agents, metal soaps, hydrotalcites, triazine ring-containing compounds, metal hydroxides, phosphate ester-based flame retardants, condensed phosphate ester-based flame retardants, phosphate-based flame retardants, inorganic phosphorus-based flame retardants, (poly)phosphate salt-based flame retardants, halogen-based flame retardants, silicon-based flame retardants, antimony oxides such as antimony trioxide, other inorganic-based flame retardant aids, other organic-based flame retardant aids, fillers, dyes, lubricants and foaming agents may be added to the near-infrared absorbing synthetic resin composition of the present invention.

Examples of the above-mentioned triazine ring-containing compounds may include melamine, ammeline, benzoguanamine, acetoguanamine, phthalodiguanamine, melamine cyanurate, melamine pyrophosphate, butylene diguanamine, norbornene diguanamine, methylene diguanamine, ethylene dimelamine, trimethylene dimelamine, tetramethylene dimelamine, hexamethylene dimelamine, 1,3-hexylenedimelanmine and the like.

Examples of the above-mentioned metal hydroxides may include magnesium hydroxide, aluminum hydroxide, calcium hydroxide, barium hydroxide, zinc hydroxide, KISUMA 5A (magnesium hydroxide: manufactured by Kyowa Chemical industry Co., Ltd.) and the like.

Examples of the above-mentioned phosphate ester-based flame retardants may include trimethyl phosphate, triethyl phosphate, tributyl phosphate, tributoxyethyl phosphate, trischloroethyl phosphate, trisdichloropropyl phosphate, triphenyl phosphate, tricresyl phosphate, cresyl diphenyl phosphate, trixylenyl phosphate, octyl diphenyl phosphate, xylenyl diphenyl phosphate, trisisopropyl phenyl phosphate, 2-ethylhexyl diphenyl phosphate, t-butylphenyl diphenyl phosphate, bis-(t-butylphenyl)phenyl phosphate, tris-(t-butylphenyl)phosphate, isopropyl phenyl diphenyl phosphate, bis-(isopropylphenyl)diphenyl phosphate, tris-(isopropylphenyl)phosphate and the like.

Examples of the above-mentioned condensed phosphate ester-based flame retardants may include 1,3-phenylenebis(diphenyl phosphate), 1,3-phenylenebis(dixylenyl phosphate), bisphenol A bis(diphenyl phosphate) and the like.

Examples of the above-mentioned (poly)phosphate salt-based flame retardants may include ammonium salts and amine salts of (poly)phosphoric acids such as ammonium polyphosphate, melamine polyphosphate, piperazine polyphosphate, melamine pyrophosphate and piperazine pyrophosphate.

Examples of the above-mentioned other inorganic-based flame retardant aids may include inorganic compounds such as titanium oxide, aluminum oxide, magnesium oxide, hydrotalcites, talc and montmollironite, and surface-treated products thereof, and examples of commercially available products may include TIPAQUER-680 (titanium oxide: manufactured by Ishihara Sangyo Kaisha, Ltd.), KYOWAMAG 150 (magnesium oxide: manufactured by Kyowa Chemical industry Co., Ltd.), DHT-4A (hydrotalcite: manufactured by Kyowa Chemical industry Co., Ltd.), ALCAMIZER 4 (zinc-modified hydrotalcite: manufactured by Kyowa Chemical industry Co., Ltd.) and the like.

Examples of the above-mentioned other organic-based flame retardant aids may include pentaerythritol.

Furthermore, where necessary, additives that are generally used in synthetic resins such as crosslinking agents, antifogging agents, plate-out preventing agents, surface treating agents, plasticizers, lubricants, flame retardants, antifogging agents, fluorescent agents, anti-mold agents, bactericides, foaming agents, metal inactivators, mold release agents, pigments, processing aids, antioxidants, light stabilizers and the like can be incorporated in the near-infrared absorbing synthetic resin composition of the present invention to the extent that the effect of the present invention is not impaired.

In the case when the boron compound represented by the above-mentioned general formula (I) and optional additives other than the above-mentioned synthetic resin are used in the near-infrared absorbing synthetic resin composition of the present invention, although the use amount thereof can be suitably selected depending on the kinds of the additives, and the like, it is preferable that the use amount is adjusted to 20 parts by mass or less in total with respect to 100 parts by mass of the synthetic resin from the viewpoint of avoidance of the impairment of the effect of the present invention.

The near-infrared absorbing synthetic resin composition of the present invention can be formed into a molded article as a near-infrared absorbing material by molding. The molding method is not specifically limited, and extrusion processing, calendar processing, injection molding, rolling, compression molding, blow molding and the like may be exemplified, and molded products having various shapes such as resin plates, sheets, films, fibers and profiles can be produced.

Alternatively, near-infrared absorbing films can be formed as near-infrared absorbing materials by dissolving the near-infrared absorbing synthetic resin composition of the present invention in various solvents and preparing cast films.

The near-infrared absorbing material obtained by the near-infrared absorbing synthetic resin composition of the present invention is excellent in near-infrared ray absorbability.

The near-infrared absorbing synthetic resin composition and near-infrared absorbing material of the present invention can be used in various applications for which near-infrared absorbability (heat ray absorbability) is required such as optical information recording materials such as optical cards, organic photoconductors, laser heat transfer recording materials, laser thermosensitive recording materials and materials for laser direct plate making; various optical filters for absorbing near-infrared ray such as filters for plasma displays, optical filters for thin displays and optical filters for photosemiconductor devices; heat ray shielding materials, heat ray shielding films and heat ray shielding resin glasses; thermal insulation-thermal storage fibers; protective eyeglasses, agricultural films, interior and exterior materials for automobiles, sheets and other various resin-molded articles; and secret inks, coating materials, and the like.

EXAMPLES

Hereinafter the present invention will further be explained in more detail with referring to Examples and the like. In the following Examples and the like, unless otherwise indicated, % and ppm are based on mass.

Example 1

Synthesis of Compound No. 1

0.6 ml (6.6 mmol) of aniline, 40 ml of bromobenzene and 2.1 g (19 mmol) of diazabicyclooctane were added to a 100 ml four-necked flask and stirred in argon. Thereafter, 4.8 ml (4.8 mmol) of a 1 mol/l toluene solution of titanium tetrachloride was added dropwise. After the dropwise addition was completed, 0.55 g (2.1 mmol) of indigo was added and reacted under a reflux state for 10 hours. After the reaction was completed, acetone was added, filtration was conducted, and the filtrate was concentrated to give a green powder. This was subjected to oil-water separation with dichloromethane and water, and the organic phase was concentrated to give 0.5 g of Intermediate-1 having the following structure as a navy blue powder (yield 58%).

[Chemical Formula 12]

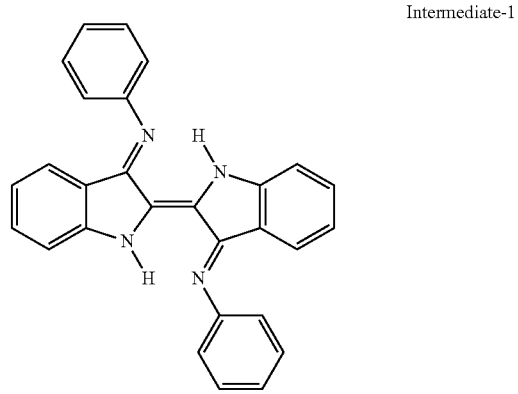 [SMILES: c1ccc(/N=C2/C(=C3\Nc4ccccc4\C3=N/c3ccccc3)Nc3ccccc32)cc1]

Intermediate-1

0.2 g (0.5 mmol) of the obtained Intermediate-1, 0.24 g (1.05 mmol) of 2-aminoethyl diphenylborinate, 0.38 g (0.38 mmol) of titanium tetrachloride and 50 ml of toluene were heated in a three-necked flask under a nitrogen atmosphere for 2 hours under reflux. The reactant was cooled to room temperature, methanol was added thereto, and filtration was conducted to give 0.1 g of a navy blue crystal powder.

For the obtained navy blue crystal powder, an FT-IR measurement and a $^1$H-NMR measurement were conducted. The result of the analysis by the FT-IR measurement is shown below, and the result of the analysis by the $^1$H-NMR measurement is shown in [FIG. 1]. By these measurement results, the obtained powder was identified as Compound No. 1 having the following structural formula.

[Chemical Formula 13]

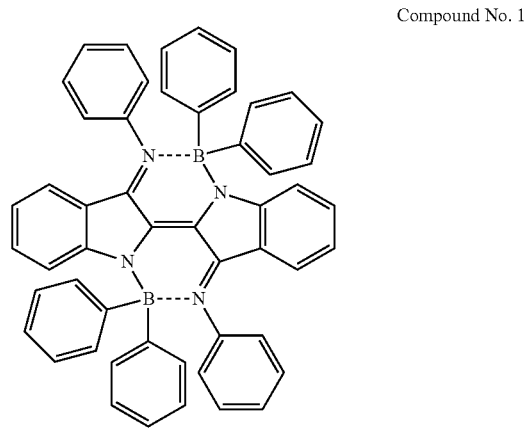

Compound No. 1

Result of FT-IR Measurement (cm$^{-1}$)
3448, 1685, 1639, 1608, 1577, 1531, 1492, 1473, 1454, 1431, 1381, 1330, 1300, 1207, 1126, 1072, 1022, 983, 864, 744, 694

Figure 2:
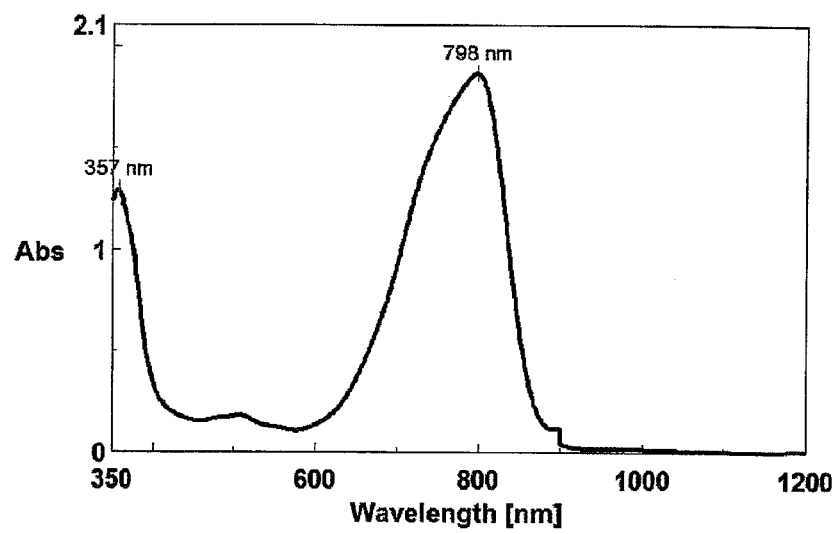
FIG. 2 shows the absorption spectrum of an acetone solution of Compound No. 1, which is a novel boron compound of the present invention synthesized in Example 1.

Furthermore, the absorption spectrum of an acetone solution of the obtained Compound No. 1 (concentration 8 mw %) was measured. The measurement was conducted by V-670 manufactured by JASCO Corporation. The absorption spectrum is shown in [FIG. 2]. The maximum absorption wavelength was 798 nm, and the molar absorption coefficient $\epsilon=1.8\times10^4 \text{ mol}^{-1} \text{ cm}^{-1}$.

Example 2

Figure 3:
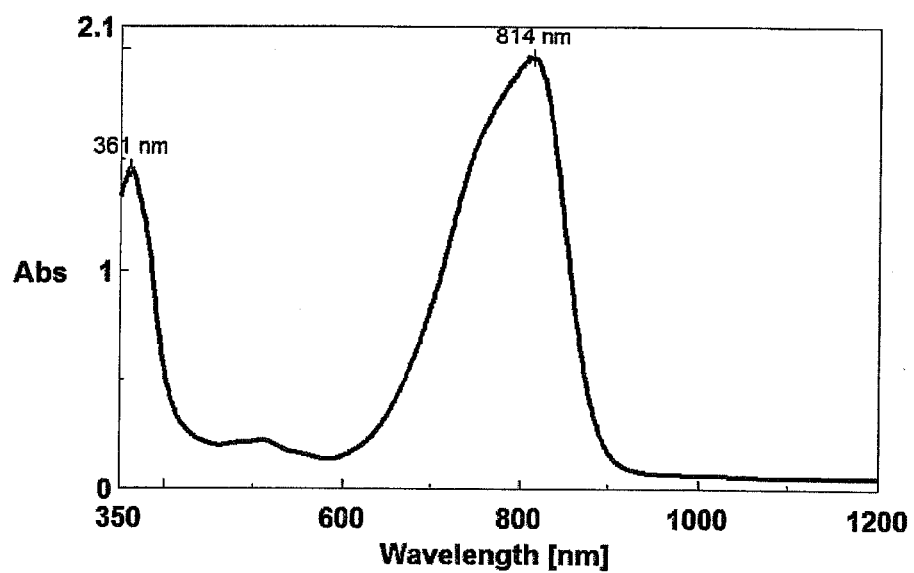
FIG. 3 shows the absorption spectrum of a polycarbonate near-infrared absorbing film, which is a near-infrared absorbing material using the near-infrared absorbing synthetic resin composition of the present invention produced in Example 2.

Production of Near-Infrared Ray Absorbing Synthetic Resin Composition and Near-Infrared Ray Absorbing Material 1.25 g of polycarbonate (EUPILON S-3000F (manufactured by Mitsubishi Engineering-Plastics Corporation)), 12.5 mg of Compound No. 1 obtained in Example 1 and dichloromethane were put into a 100 ml measurement flask, sufficiently dissolved, and diluted in a measuring cylinder to 100 ml to thereby give a solution of the near-infrared ray absorbing synthetic resin composition. 10 ml of this solution was taken into a Petri dish and slowly dried to give a polycarbonate near-infrared ray absorbing film, which is a near-infrared ray absorbing material. The obtained film had a thickness of 90 μm. Furthermore, an absorption spectrum of the obtained polycarbonate near-infrared ray absorbing film was measured. The measurement was conducted by V-670 manufactured by JASCO Corporation. The absorption spectrum is shown in [FIG. 3]. The obtained film had a maximum absorption wavelength at 814 nm and a molar absorption coefficient in terms of Compound No. 1 of $\epsilon=1.6\times10^4 \text{ Mol}^{-1} \text{ cm}^{-1}$, and thus it was confirmed that this film shows fine absorption in the near-infrared range.

Example 3

Production of Near-Infrared Ray Absorbing Synthetic Resin Composition and Near-Infrared Ray Absorbing Material A PMMA near-infrared ray absorbing film, which is a near-infrared ray absorbing material, was obtained in a similar manner to Example 2, except that polymethyl methacrylate (PMMA) was used instead of polycarbonate, and that the thickness of the film was 30 μm. The obtained film had a maximum absorption wavelength at 813 nm and a molar absorption coefficient in terms of Compound No. 1 of $\epsilon=1.6\times10^4 \text{ Mol}^{-1} \text{ cm}^{-1}$, and thus it was confirmed that this film shows fine absorption in the near-infrared range.

Evaluation Example 1

The Haze values (transparency) of the near-infrared ray absorbing films obtained in Examples 2 and 3 were measured in reference to JISK7105. Measurements were also conducted on a polycarbonate film (Comparative Example 1), which was prepared in a similar manner to Example 2 except that Compound No. 1 was not used, and on a PMMA film (Comparative Example 2), which was prepared in a similar manner to Example 3 except that Compound No. 1 was not used. The results of the measurements are shown in [Table 1].

TABLE 1

|  | Example 2 | Comp. Example 1 | Example 3 | Comp. Example 2 |
|---|---|---|---|---|
| Test Compound | Compound No.1 | None | Compound No.1 | None |
| Transparency Haze values (%) | 1.5 | 1.1 | 1.5 | 1.2 |

It was confirmed from the results in the above-mentioned [Table 1] that the boron compound of the present invention does not deteriorate the transparency of the synthetic resin and does not affect the inherent color of the resin.

The invention claimed is:
1. A boron compound represented by the following general formula (I):

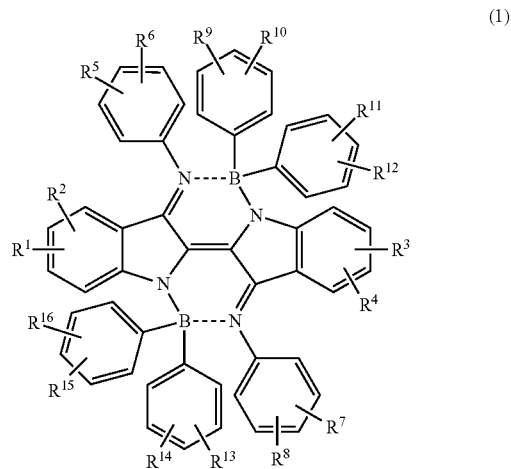

wherein $R^1$ to $R^{16}$ may be the same or different from each other, and each represent a hydrogen atom, a halogen atom, a nitro group, a cyano group, an amino group, an alkyl group having 1 to 20 carbon atoms optionally having substituents, an aryl group having 6 to 20 carbon atoms optionally having substituents, an alkoxy group having 1 to 20 carbon atoms optionally having substituents, an aryloxy group having 6 to 20 carbon atoms optionally having substituents, an arylalkyl group having 7 to 20 carbon atoms optionally having substituents, a cycloalkyl group having 5 to 12 carbon atoms optionally having substituents, an alkylthio group having 1 to 20 carbon atoms optionally having substituents, an arylthio group having 6 to 20 carbon atoms optionally having substituents, an alkylamino group having 1 to 20 carbon atoms optionally having substituents, or an arylamino group having 6 to 20 carbon atoms optionally having substituents, wherein the adjacent two groups of the groups represented by $R^1$ to $R^{16}$ may link to form a 5-membered ring or a 6-membered ring together with the carbon atom to which the respective two groups are binding.

2. A near-infrared absorber containing the boron compound according to claim 1.

3. A near-infrared absorbing synthetic resin containing the boron compound according to claim 1.

4. A near-infrared absorbing material formed of the near-infrared absorbing synthetic resin composition according to claim 3.

* * * * *